United States Patent [19]

Flesher

[11] Patent Number: 4,532,805
[45] Date of Patent: Aug. 6, 1985

[54] PIPETTE SYSTEM

[76] Inventor: Robert W. Flesher, 1836 Circle Rd., Towson, Md. 21204

[21] Appl. No.: 615,070

[22] Filed: May 29, 1984

[51] Int. Cl.³ ................................................ B01L 3/02
[52] U.S. Cl. .............................. 73/863.32; 73/864.01; 73/864.11; 73/864.15
[58] Field of Search ........... 73/863.32, 864.02, 864.11, 73/864.15; 422/100

[56] References Cited

U.S. PATENT DOCUMENTS

| | | | |
|---|---|---|---|
| 3,572,552 | 3/1971 | Guinn | 222/263 |
| 3,807,235 | 4/1974 | Lefkovits et al. | |
| 3,982,438 | 9/1976 | Byrs | |
| 4,047,438 | 9/1977 | Sekine | |
| 4,158,035 | 6/1979 | Haase et al. | 422/100 |
| 4,461,328 | 7/1984 | Kenney | 73/864.02 |

*Primary Examiner*—S. Clement Swisher
*Attorney, Agent, or Firm*—John F. McClellan, Sr.

[57] ABSTRACT

A multi-pipette system of the type having sample volume determined by size of cavities into which flexible membrane portions are drawn, provides a microporous block with the cavities formed in it for drawing the flexible membrane into the cavities when pressure is reduced above the microporous block. Slide-in-place location and replacement is provided for supply containers, disposable tube arrays for drawing up samples and for expelling them, and for flexible membranes. In an embodiment microporous block cavity size is adjustable.

23 Claims, 8 Drawing Figures

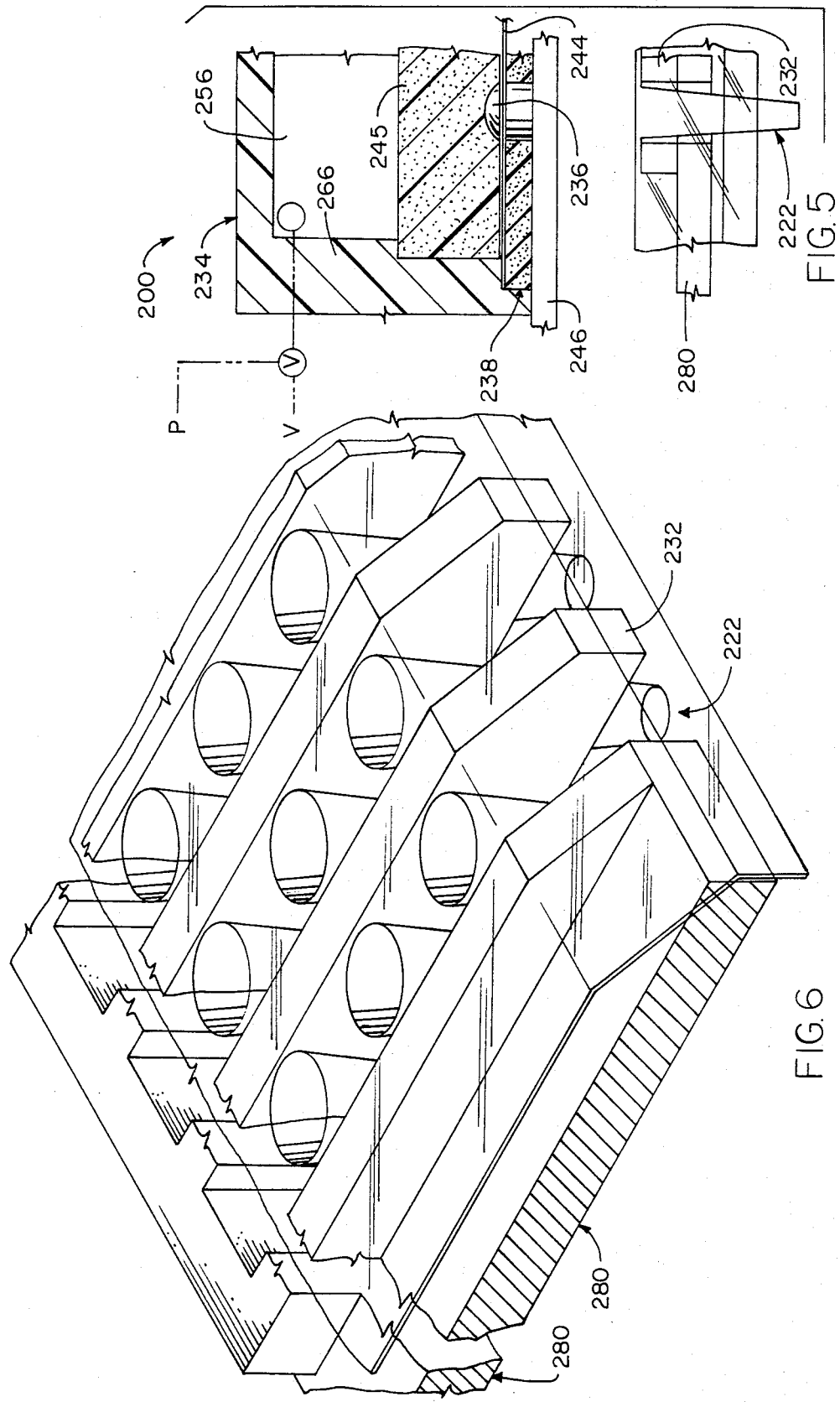

PIPETTE SYSTEM

FIELD OF THE INVENTION

This invention relates generally to fluid handling, and specifically to a system for transferring at the same time a plurality of liquid samples.

BACKGROUND OF THE INVENTION

In the prior art, disclosures of pipetting systems appear in various U.S. Patents:

U.S. Pat. No. 3,572,552 to P. W. Guinn, 3-30-71, disclosed an externally calibrated form of dispenser employing deflectable diaphragm communicating with a plurality of tips; gas or liquid was employed;

U.S. Pat. No. 3,807,235 to I. Lefkovits and O. Kamber, 4-30-74, disclosed vacuum actuation of a diaphragm to draw it into hemispherical chambers defining volume drawn into respective cannulas;

U.S. Pat. No. 3,982,438 to W. J. Byrd, 9-28-76, disclosed a system analogous to the Lefkowitz and Kamber system with positive and negative pressure actution of the diaphragm and hemispherical recesses below as well as above the diagram;

U.S. Pat. No. 4,047,438 to T. Sekine, 9-13-77, disclosed a system in which local hemispherical convolutions of the flexible diaphragm were permanent and were forcibly flattened to actuate the system;

U.S. Pat. No. 4,158,035 to T. Haase and W. Byrd, 6-12-79, disclosed a further system with hemispherical recesses both above and below the flexible diaphragm.

SUMMARY OF THE INVENTION

None of the above-disclosed systems nor any other is believed to have become the standard of commerce for the purpose, and to provide a system that can become such is a principal object of this invention.

Another object is to provide a system in which a flexible membrane is uniformly drawn into a cavity by provision of the cavity.

Further objects are to provide a system that is low-cost but inherently accurate, that is volume adjustable, easy to make, and is easy and inexpensive to clean in the event of contamination.

Still further objects are to provide a system as described that is easy to learn to use and is simple and safe to use, that requires a minimum of connecting lines for operation, that is compact and lightweight, that is versatile in that it can be made in a variety of sizes, and is durable.

A multi-pipette system of the type having sample volume determined by size of cavities into which flexible membrane portions are drawn, provides a microporous block, with the cavities formed in it, for drawing the flexible membrane into the cavities when pressure is reduced above the microporous block. Slide-in-place location and replacement is provided for supply containers, for disposable tube arrays for drawing up samples and for expelling them, and for flexible tube-isolating membranes. In an embodiment cavity size is adjustable.

The above and other objects and advantages of this invention will become more readily apparent on examination of the following description, including the drawings in which like reference numerals refer to like parts. The drawings are made to various scales, for better exposition.

FIG. 5 is a fragmentary elevational diagram, partly in section;

FIG. 6 is a fragmentary perspective detail partly in section, of a tube-array supporting portion;

DETAILED DESCRIPTION

Figure 1:
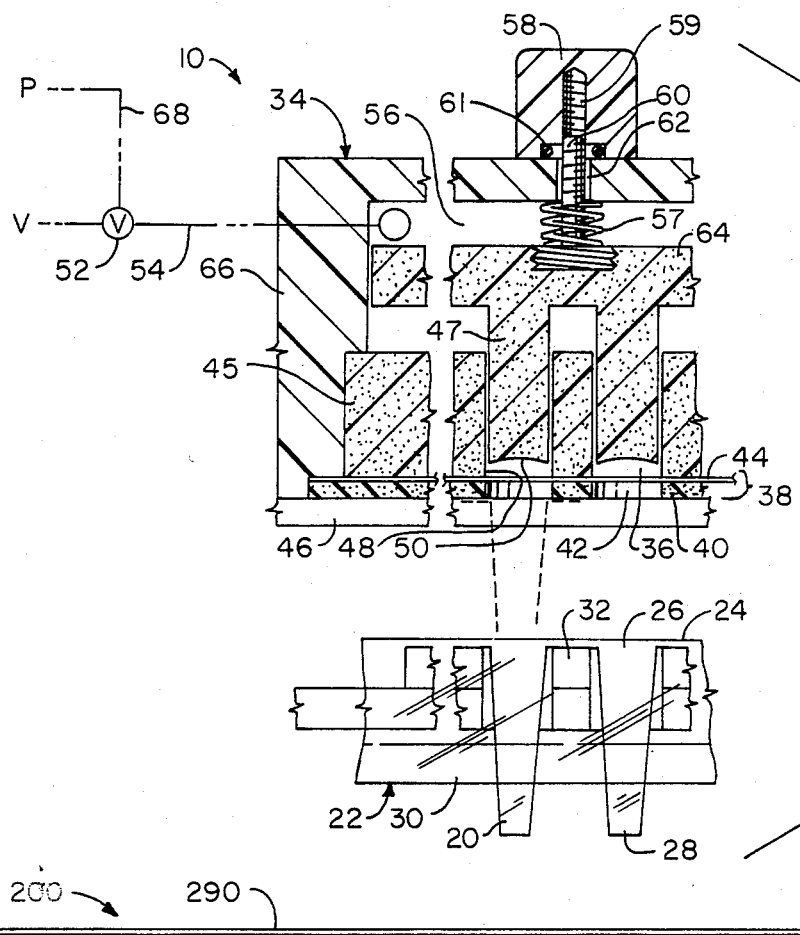
FIG. 1 is a fragmentary partly sectional front elevational diagram of a first embodiment.

FIG. 1 diagrams an embodiment 10 of the invention. Spacing is exaggerated for exposition.

At the bottom are shown two tubes 20 of a planar array 22 of clear plastic truncate cone-shaped tubes held together by a planar portion 24 between the tubes and integral with the larger ends of the tubes. Both ends 26, 28 of the tubes 20 are open. Vacu-formed disposable integral integral arrays 22 are provided, the shape helping the forming. A downward extension 30 of the portion 24 may be used as a handle for sliding the array of tubes into the position shown, suopported by fixed fingers 32.

To draw an equal-volume sample of liquid into each of the tubes 20 for transfer by subsequent ejection from the tubes into respective containers, the tubes are first raised relative to manifold body structure 34 above them, until each tube is directly below a respective cavity 36 of a plurality of cavities equal in number to the number of tubes (96 preferred) in the array 22 of tubes.

Separating the tubes 20 from the cavities 36 in the raised position (broken lines) is a resiliently flexible membrane assembly 38 against which the fingers 32 as a group hermetically clamp the array of tubes. The flexible membrane assembly 38 is shown exaggerated in thickness, for exposition.

The flexible membrane assembly 38 comprises preferably two layers cemented together. The bottom layer 40 has holes 42 through it in axial correspondence with the upper ends of the tubes and the cavities. It may be resiliently compressible closed-cell neoprene foam about 1/16 inch (15 mm) thick. The top layer 44 is preferably an impervious latex membrane, that may be 0.007 inch (0.2 mm) thick. A frame 46 holds the flexible membrane in place. Suitable microporous material such as porous polyethylene at 45, 47 defines each cavity structure, which in this embodiment includes a cylindrical bore 48 and a cylindrical plunger 50 with a spherically concave end extending into the bore.

In operation, with the lower ends of the tubes 20 respectively dipped in the liquid or liquids to be sampled and with the upper ends of the tubes (the upper face of the tubular array 22) clamped against the undersurface of the flexible membrane assembly 38, valve 52 is operated to reduce pressure through line 54 and in space 56 within manifold structure 34. Ambient air drawn through the porous material partially evacuates each of the cavities 36, uniformly raising adjacent parts of the latex membrane into fitting contact within the cavities and drawing liquid samples into the tubes 20. The uniform action of this provision is effective in prevention of distortion of the membrane by "vacuum dead-spots" and is economical to make as well as precise in operation.

Volume of liquid drawn into the tubes depends on setting of knob 58. The knob rests on the exterior of manifold structure 34 and by means of a threaded bore 59 in the knob engages screw 60 that passes from the manifold space 56 through a hole 62. A gasket 61 under the knob prevents leakage at the hole, and a spring 57 opposes the knob by biasing the screw downwardly. Screw 60 is fixed to plate 64 by any suitable means, and setting the height of the screw sets the height of the plate and the plungers 47 extending downward from it. Like the other portion 45 defining the cavities, the plungers, and the plate 64 that is integral with them, are preferably of rigid blocks of the microporous material. The exterior walls 66 may be of any suitable impervious thermoplastic or may be of metal such as aluminum.

To expel the liquid from the tubes into a second or receiving container-array, replacing a first, or supply container-array (neither shown in this Figure but appearing in later Figures) the valve is operated to release the partial vacuum in the manifold space, permitting the latex membrane to snap back. If desired, air pressure may be applied through a suitable line 68 to accelerate the snap-back.

Figure 2:
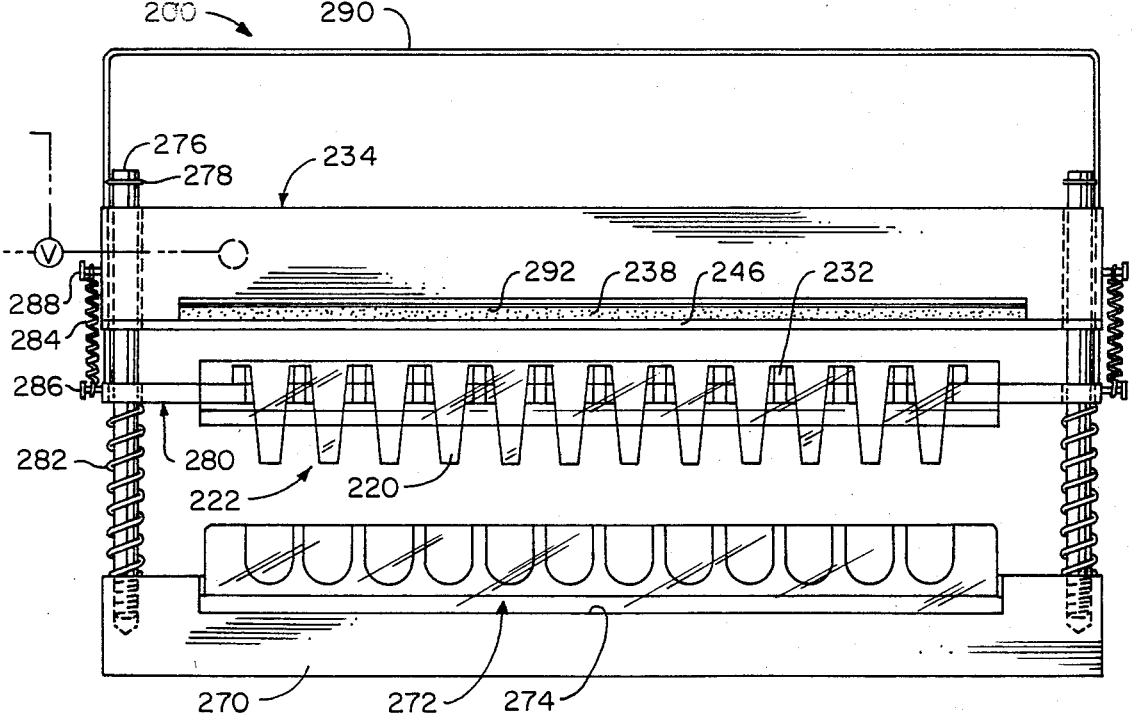
FIG. 2 is a front elevational view of a second embodiment.

FIG. 2 shows a front elevational view of the system in a second embodiment 200, like the first embodiment except that there is no cavity-size adjustment; cavity size is a fixed constant.

Base 270 supports the array 272 of supply or of receiving containers in a recess 274. The first or sample supply array or the second or sample receiving array may be the same in structure, and may be tray-like.

A way system arises from the base 270; this may comprise four parallel rods 276 screwed into the base near the corners. Snaprings 278 at the top prevent overtravel of the components slidable along the rods, namely the member 280 integrally fixed to the fingers 232 that support the array 222 of tubes, and the manifold structure 234. Respective compression springs 282 on the lower parts of the rods support the member 280, with the parallel fingers 232 that in turn support the array 222 of tubes 220.

The array of tubes is shown in a low position for being slidably inserted or else removed after use for replacement with a new array. When in use-position, the fingers 232 clamp the array 222 of the tubes 220 up against the flexible membrane assembly 238 under upward bias of the tension springs 284, that are attached at the lower end to screws 286 on the member 280 and at the upper end to screws 288 on the manifold structure 234. Cam structure, operated by arm 290 located across the top of the system from side to side and, as will be seen, affixed pivotally to the manifold structure, is forcing apart the member 280 and the manifold structure 234 in the position shown. Details appear later of this provision for easy loading and unloading of the array 222.

Flexible membrane assembly 238 slides out of slot 292 above frame 246 for replacement when desired.

The system is substantially symmetrical about the centerline.

Figure 3:
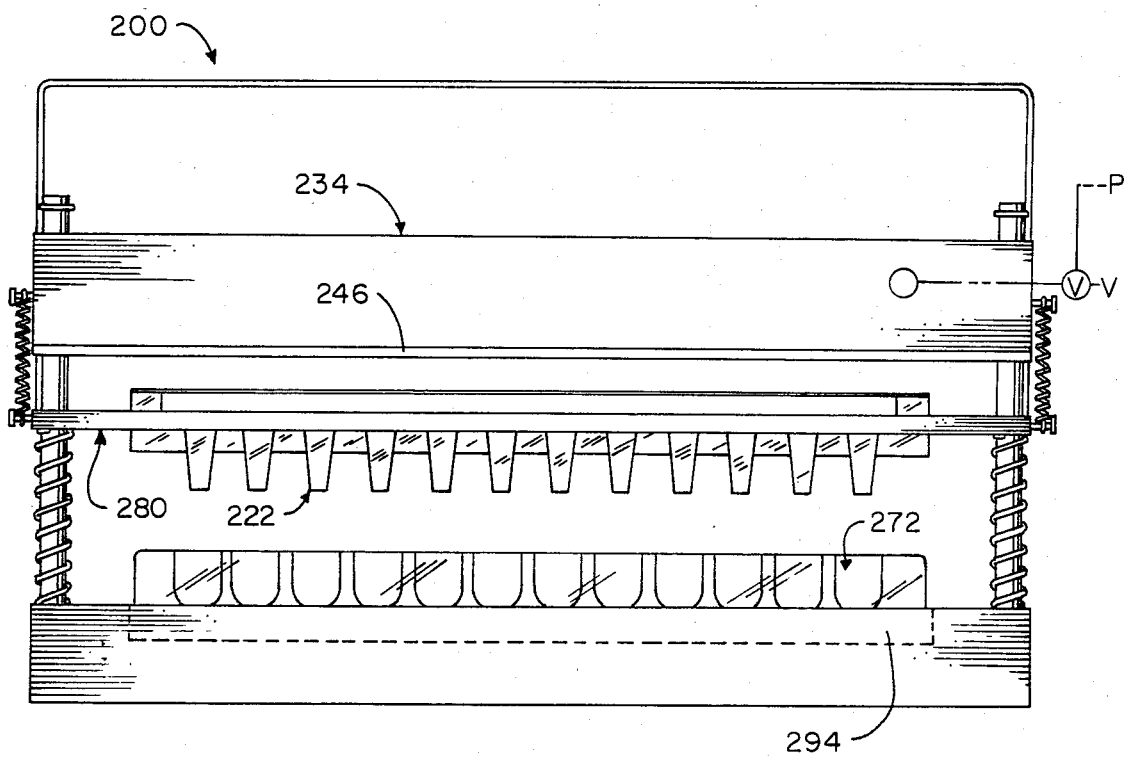
FIG. 3 is a rear elevational view thereof.

FIG. 3 shows the second embodiment 200 rear view, similar to the front view except that a flange 294 across the back stops the sliding position of container arrays, 272 shown, at the proper point. The containers are of conventional design. A similar flange is not needed for the array of tubes 222. The comb-like member 280 is preferably proportioned to engage the tubes at the proper sliding position, as shown later.

The frame appears at 246. It may be detachably screwed to the manifold structure 234.

Figure 4:
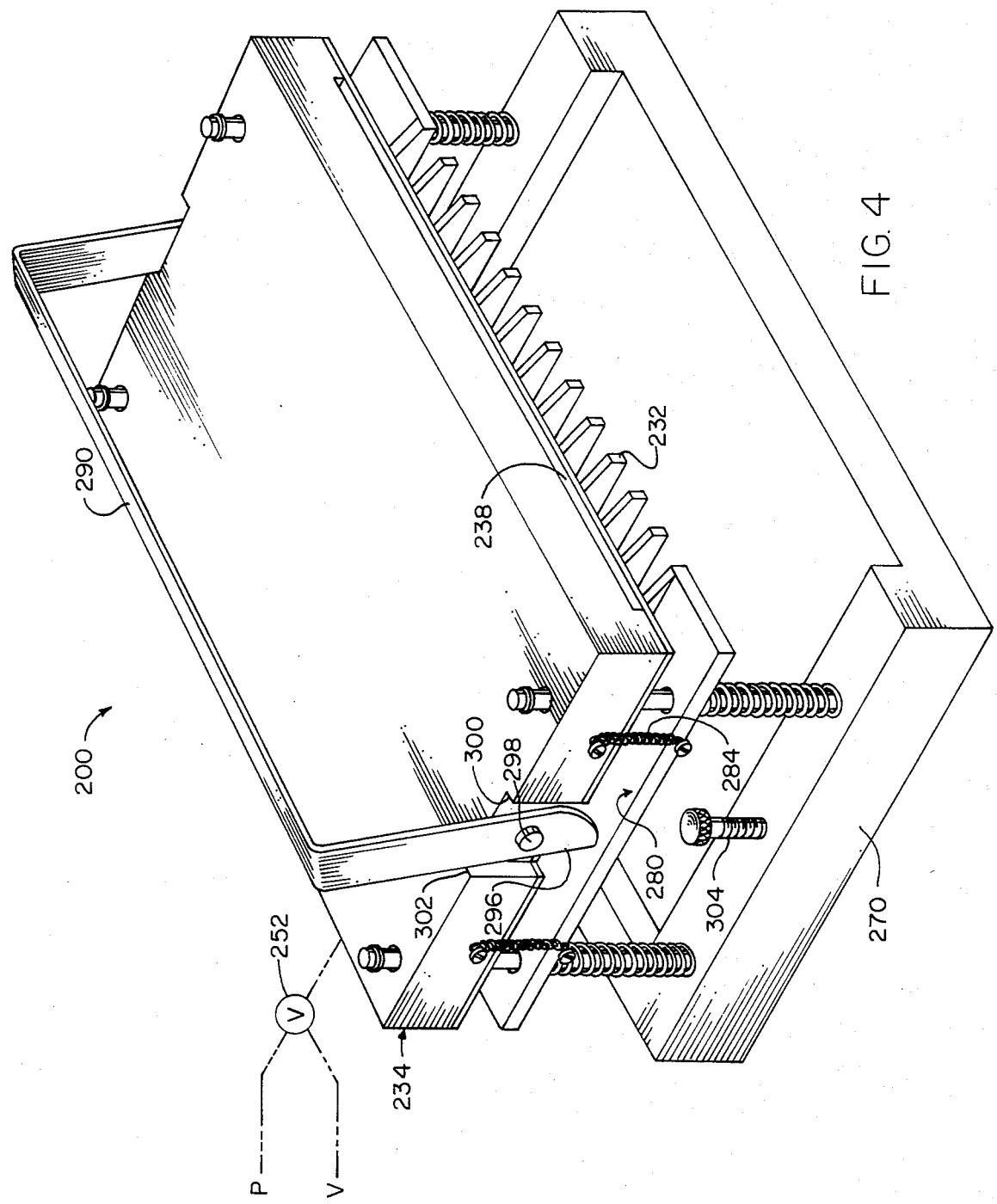
FIG. 4 is a top perspective view thereof.

FIG. 4 shows the second embodiment 200 in perspective.

Manipulation is simple:

(1) Insert a container in the recess in the base 270. (The recess automatically insures proper position).

(2) Push the handle 290 to the rear. (This pivots the cam ends, 296 shown, about the respective pivot pins, 298 shown, and by pressing on member 280, separates member 280 from the flexible membrane against the bias of springs 284. The edges 300, 302 of the slots in the sides of the manifold structure may advantageously coact as stops for cam positioning.)

(3) Slide a new array of tubes in place over the fingers 232. (The tapered front ends of the fingers can assist this.)

(4) Pull the handle to the front and (5) press down on it. (This clamps the array of tubes against the flexible membrane assembly 238, and positions the tips of the tubes in the container below.)

(5) Operate the valve 252 to drawn in or to expel the sample liquid as desired.

On each side a stop-screw 304 with a knurled head provides ready adjustment of downward travel of manifold 234 and tube array held by member 280.

FIG. 5 diagrams details of the second or fixed-volume embodiment 200, preferred for simplicity. The manifold space 256 in manifold 234 is simply a cavity with no moving parts defining it. It is bounded on the top, sides, back and front, by impermeable walls 266 and is bounded on the bottom by microporous block 245.

Cavities 236 are closed by the latex layer 244 of the flexible membrane assembly 238 against which the fingers 232 of member 280 can clamp the array 22 of tubes. The frame appears at 246.

FIG. 6 details a preferred relation of the fingers 232 of member 280 to the array 222 of tubes. Comblike member 280 contacts the array of tubes slid into position on it and stops travel of the array at the correct position.

Figure 7:
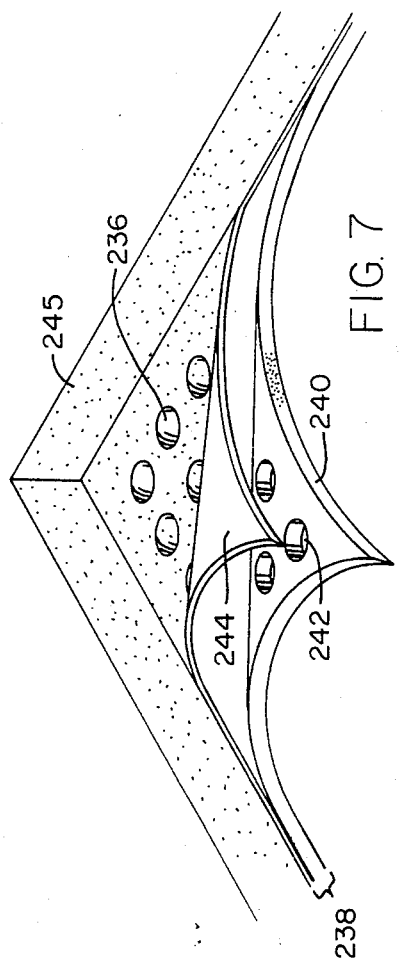
FIG. 7 is a bottom perspective fragmentary diagram on an exaggerated scale showing flexible membrane details.

FIG. 7 shows the relation of the microporous block 245 with cavities 236 (of embodiment 200) to the latex layer 244 and the foam neoprene layer 240 with holes 242, of the flexible membrane assembly 238.

Figure 8:
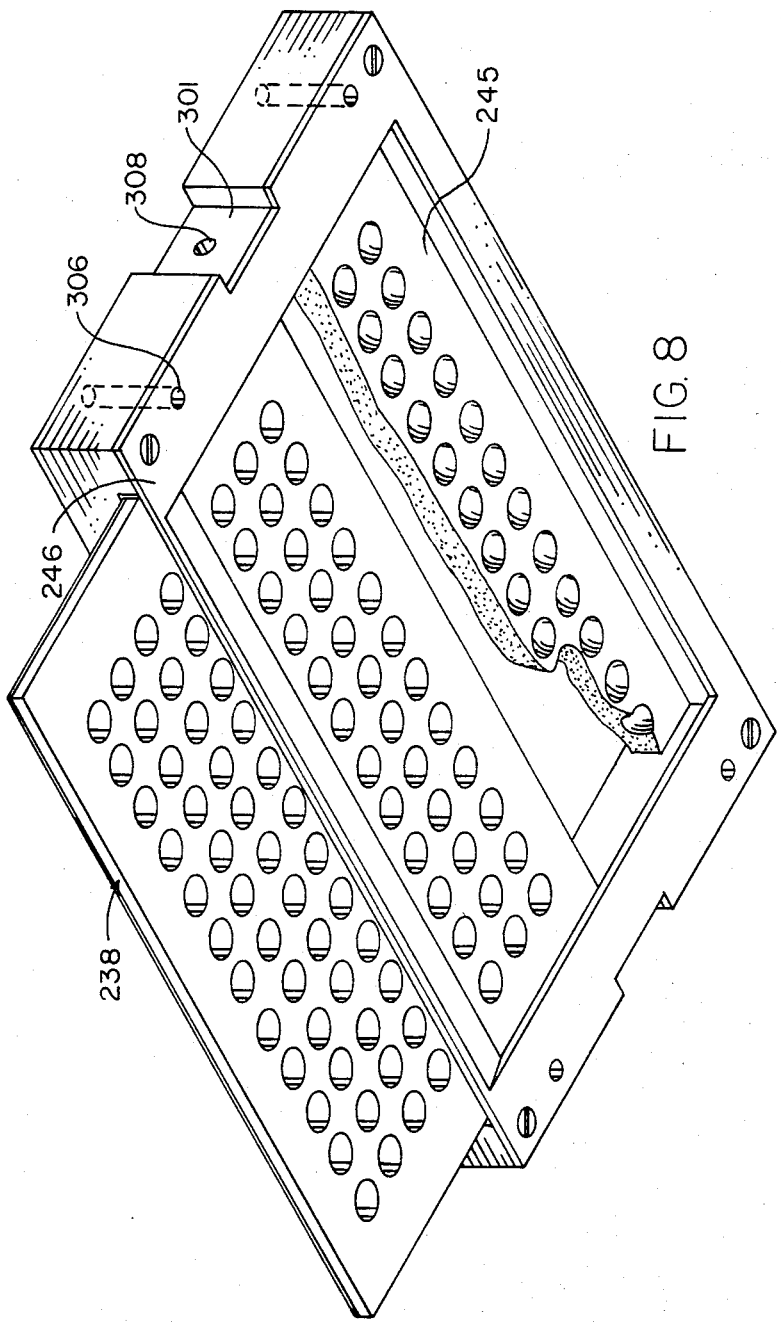
FIG. 8 is a fragmentary perspective detail of a porous plate with cavities and the flexible membrane associated therewith.

FIG. 8 shows the relation of the frame 246 supporting the flexible membrane assembly 238 as it slides in or out, and the microporous block 245 above it, for embodiment 200. Holes 306 are for the rods of the way system. Holes 308 in the slots 301 are for the cam handle pivot pins.

The effective thickness may be about 0.25 to 0.5 inch (10 to 20 mm), as for block 245, FIG. 5; with other embodiments proportional. The part may be molded for volume production or individually machined from a block.

The porous thermoplastic polymer may have a void ratio of 40% to 60%, and is obtainable from Glassrock Products, Inc., Porex Division, Fairburn, Ga., 30213.

A medium grade of Chrysler OILITE (TM) sintered bronze without the oil is an example of suitable microporosity as well as suitable sintered metal.

The disposable vacuformed tube arrays may be of rigid PVC, 0.012 inch (0.3 mm) thick. Other material such as polyethylene, preferably bio-degradable, may also be suitable.

In conclusion, the overall efficiency, simplicity and economy of this invention will be apparent when compared with other known art.

This invention is not to be construed as limited to the particular forms disclosed herein, since these are to be regarded as illustrative rather than restrictive. It is, therefore, to be understood that the invention may be practiced within the scope of the claims otherwise than as specifically described.

What is claimed and desired to be protected by U.S. Letters Patent is:

1. In a system for micropipetting having:
   means for transferring a plurality of liquid samples from a first plurality of containers into a plurality of tubes using a fluid exhaust
   and for discharging said plurality of liquid samples from the plurality of tubes into a second plurality of containers, including:
   the means for transferring including structure defining a plurality of cavities,
   a flexible membrane located for sealing between said plurality of tubes and plurality of cavities, and
   means for removing ambient fluid from said plurality of cavities and drawing said flexible membrane thereinto and said liquid into said plurality of tubes, the improvement comprising: the means for removing including said structure defining the plurality of cavities comprising microporous structure, and valving means for communicating the microporous structure with a fluid exhaust.

2. In a system as recited in claim 1, said microporous structure being of porous thermoplastic material.

3. In a system as recited in claim 1, siad microporous structure being a substantially rigid block of porous polyethylene, 4. In a system as recited in claim 1, a manifold associating, through said microporous structure, the valving means with the plurality of cavities.

5. In a system as recited in claim 1, the microporous structure having a lower surface, said plurality of cavities being in the lower surface, and means for holding the flexible membrane against said lower surface.

6. In a system as recited in claim 5, said means for holding including a frame for slidably receiving the flexible membrane.

7. In a system as recited in claim 1, the flexible membrane including substantially impervious material.

8. In a system as recited in claim 1, the flexible membrane including resiliently compressible material.

9. In a system as recited in claim 1, the flexible membrane including a layer of substantially impervious material and a layer of resiliently compressible material.

10. In a system as recited in claim 1, means for adjusting volume of liquid samples transferred including means for adjusting volume of said plurality of cavities.

11. In a system as recited in claim 10, the means for adjusting volume comprising: each of the cavities including a bore portion, a plunger extending into each bore portion, and means for adjusting extension of the plungers into the bore portions.

12. A system as recited in claim 11, a plate mounting the plungers, and the means for adjusting, adjusting position of the plate axially of the bore portion.

13. In a system as recited in claim 12, said plate and plungers being of microporous material.

14. In a system as recited in claim 12, said plungers having respective concave ends.

15. In a system as recited in claim 12, said adjustment including a screw associated with said plate in a manifold space, the screw passing out of the manifold space through a hole, a knob on the screw, and means for sealing the hole.

16. In a system as recited in claim 1, the plurality of tubes having truncated-cone shape with smaller end down, and a planar member integral with the tubes at the larger end of the tubes.

17. In a system as recited in claim 16, means for clamping the plurality of tubes, larger end up, against the flexible membrane, with the tubes aligned with the cavities.

18. In a system as recited in claim 17, the clamping means including a manifold body; a member with a plurality of fixed parallel fingers, spaced for slidably receiving the plurality of tubes therebetween for supporting the plurality of tubes, means for biasing said member toward the manifold body, and means for holding apart the member and the manifold body against said biasing, for insertion and removal of the plurality of tubes.

19. In a system as recited in claim 18, the means for holding apart including a cam.

20. In a system as recited in claim 18, means for retractably dipping a portion of the plurality of tubes into a first container, including a base for holding a first container, and a way system of the base supporting the manifold body resiliently relative to the base, whereby the manifold body and plurality of tubes can be moved towards the base.

21. In a system as recited in claim 20, and means for adjusting limiting movement of the manifold body and plurality of tubes towards the base.

22. In a system for micropipetting, of the type having structure defining a plurality of cavities, a membrane positioned from being drawn into the plurality of cavities, means for drawing the membrane into the plurality of cavities, and means connected with the membrane for metering fluid samples in proportion to the drawing of the membrane into the plurality of cavities, the improvement comprising: the structure defining the plurality of cavities being microporous structure, and a manifold associating the means for drawing with the plurality of cavities through the microporous structure.

23. In a system as recited in claim 22, the means connected including the subcombination of an array of tubes in the form of connected truncate cones, of substantially thin bio-degradable material whereby they are disposable.

* * * * *

UNITED STATES PATENT AND TRADEMARK OFFICE
CERTIFICATE OF CORRECTION

PATENT NO. : 4,532,805
DATED : AUGUST 6, 1985
INVENTOR(S) : ROBERT W. FLESHER

It is certified that error appears in the above-identified patent and that said Letters Patent are hereby corrected as shown below:

Claim 22, line 3, "from" should read -- for --.

Signed and Sealed this

Fifth Day of November 1985

[SEAL]

Attest:

Attesting Officer

DONALD J. QUIGG

Commissioner of Patents and Trademarks